US00PP29707P3

(12) United States Plant Patent
Parris et al.

(10) Patent No.: US PP29,707 P3
(45) Date of Patent: Sep. 25, 2018

(54) ***MAGNOLIA* PLANT NAMED 'MELISSA PARRIS'**

(50) Latin Name: *Magnolia hybrida*
Varietal Denomination: Melissa Parris

(71) Applicants: Blaine Childress; Kevin Parris, Spartanburg, SC (US)

(72) Inventors: Kevin Parris, Spartanburg, SC (US); Dennis Ledvina

(73) Assignee: Idelwylde Ornamentals, Spartanburg, SC (US)

( * ) Notice: Subject to any disclaimer, the term of this patent is extended or adjusted under 35 U.S.C. 154(b) by 8 days.

(21) Appl. No.: 14/999,608

(22) Filed: Jun. 3, 2016

(65) Prior Publication Data

US 2017/0354074 P1 Dec. 7, 2017

(51) Int. Cl.
*A01H 5/02* (2018.01)

(52) U.S. Cl.
USPC ..... Plt./223
CPC ..... *A01H 5/02* (2013.01)

(58) Field of Classification Search
USPC ..... Plt./223
See application file for complete search history.

*Primary Examiner* — Keith O Robinson
(74) *Attorney, Agent, or Firm* — Blaine Childress

(57) ABSTRACT

A new and distinct *Magnolia* cultivar named 'Melissa Parris' is disclosed, characterized by having pleasantly scented pink flowers, a dominant central leader, and large tardily deciduous foliage. The new variety is a *Magnolia*, normally produced as a medium to large ornamental tree.

4 Drawing Sheets

Latin name: *Magnolia hybrida.*
Varietal denomination: 'Melissa Parris'.

STATEMENT REGARDING FEDERAL SPONSORSHIP

No federal funding was involved in the research or development associated with this invention.

BACKGROUND OF THE INVENTION

The present invention relates to a new and distinct cultivar of a deciduous *Magnolia* hybrid resulting from the intentional breeding of *Magnolia* [*tripetala* x (*tripetala* x *obovata*)] 'Silk Road' with *Magnolia insignis* MGA 355, now registered as the cultivar *Magnolia insignis* 'Anita Figlar'. The objective of the breeding effort was to produce a large pink flowered *magnolia* cultivar that would flower after typical spring frosts. Pollen from harvested flowers of unpatented selection *Magnolia insignis* 'Anita Figlar', in Six Mile, S.C., was isolated and dehisced by co-inventor Parris in May 2010, and subsequently used to hand pollinate flowers of the unpatented selection *Magnolia* hybrid 'Silk Road' by co-inventor Ledvina in Green Bay, Wis. A portion of the resulting seeds from the cross were carefully collected, and thereafter germinated and planted in Spartanburd, S.C. by co-inventor Parris in 2011. The resulting new variety was grown to flowering age in full sun, and first observed to flower in May 2014. The plant was thereafter selected for propagation by co-inventor Parris in May 2015 after observing prolific, ornamental flowering that commenced after the last average frost date in the upstate of South Carolina. The present exemplar stands 20 feet (6.0 m) tall by 8 feet (2.4 m) diameter. It has demonstrated excellent hardiness, having withstood Summer temperatures of 101° F. (38° C.) and Winter low temperatures of 6° F. (−14° C.).

Asexual reproduction of the cultivar 'Melissa Parris' has been repeatedly conducted under the direction of co-inventor Parris from vegetative cuttings in Gainesville, Ga. and Spartanburg, S.C. Small rooted cuttings from the novel plant have flowered and grown with vigor, thereby demonstrating that the cultivar is stable. Co-inventor Parris has also successfully reproduced the cultivar by chip budding using in-ground and container specimens of the hybrid *Magnolia yuyuanensis* x *Magnolia insignis* as rootstock.

SUMMARY OF THE INVENTION

The cultivar 'Melissa Parris' has not been observed under all possible environmental conditions. The phenotype may vary somewhat with variations in temperature, day length, moisture availability, and light intensity, however no variance in genotype would result, as may be determined by genetic characterization, with methods such as inter-simple sequence repeat (ISSR) markers.

The following traits have been repeatedly observed and are determined to be the unique characteristics of *Magnolia* 'Melissa Parris'. These characteristics in combination distinguish 'Melissa Parris' as a new and distinct cultivar.

1. 'Melissa Parris' exhibits hybrid vigor
2. 'Melissa Parris' exhibits a dominant central leader with compact branch arrangement
3. 'Melissa Parris' exhibits large attractive glossy foliage
4. 'Melissa Parris' exhibits relatively large, lotus-like flowers
5. 'Melissa Parris' exhibits pink outer tepals having a color of RHS Red-Purple Group 65A
6. 'Melissa Parris' exhibits alternate pink and white striated inner tepals
7. 'Melissa Parris' produces a pleasant sweet citrus-like floral fragrance 8. 'Melissa Parris' exhibits late Spring to early Summer bloom

PARENT COMPARISON

Plants of the new cultivar 'Melissa Parris' exhibit intermediate characteristics between that of the seed parent, *Magnolia* hybrid 'Silk Road', and that of the pollen parent *Magnolia insignis* 'Anita Figlar'.

'Melissa Parris' retains some of the deciduous nature, large foliage, and large flowers of the seed parent, 'Silk Road', however the leaf drop is tardy in contrast, and the leaves have a darker, glossier appearance than the seed parent. The flowers of 'Silk Road' are white, while the flowers of new cultivar 'Melissa Parris' are smaller and distinctively pink with striations.

'Melissa Parris' vividly exhibits aspects of the pink/red floral pigmentation of the pollen parent, 'Anita Figlar' (RHS Red Group 53A), but in contrast produces deep pink outer tepals (RHS Red-Purple Group 65A) and alternating pink and white inner tepals. Inner tepals may be further distinguished from either parent by vein-like striations and blends of pink along a white background. 'Melissa Parris' flowers are markedly larger than the pollen parent (FIG. 4).

The seed and pollen parents are the best comparisons to the new cultivar 'Melissa Parris', as no other clonal introductions have been made from this unique cross.

BRIEF DESCRIPTION OF THE PHOTOGRAPHS

The accompanying photographs Illustrate in full color, unique aspects of 'Melissa Parris'.

DETAILED BOTANICAL DESCRIPTION

In the following description, color references are made to The Royal Horticulture Society Colour Chart, The Royal Horticulture Society, London, and Flower Council of Holland, Leiden, Copyright 1966; except where general terms of ordinary dictionary significance are used. The following observations and measurements describe 'Melissa Parris' grown outdoors in Spartanburg, S.C., USDA Zone 7B. Measurements and numerical values represent averages of typical plant features.

Botanical classification: *Magnolia* 'Melissa Parris'.

Propagation:

Time to initiate roots: About 40 days at approximately 30° C.

Time to produce a rooted cutting: About 90 days at approximately 30° C.; transplanted carefully following spring bud break at about 250 days.

Root description: Typical *Magnolia* root, thick (0.2 cm on current season's root), coarse and white (RHS 155D), aging to light yellow brown (RHS 158A) within the first season as observed in container production in South Carolina.

Time to chip bud: Spring budding proven successful on *Magnolia yuyuanensis* x *Magnolia insignis* root stock. 3-4 weeks from budding to bud break.

Figure 1:
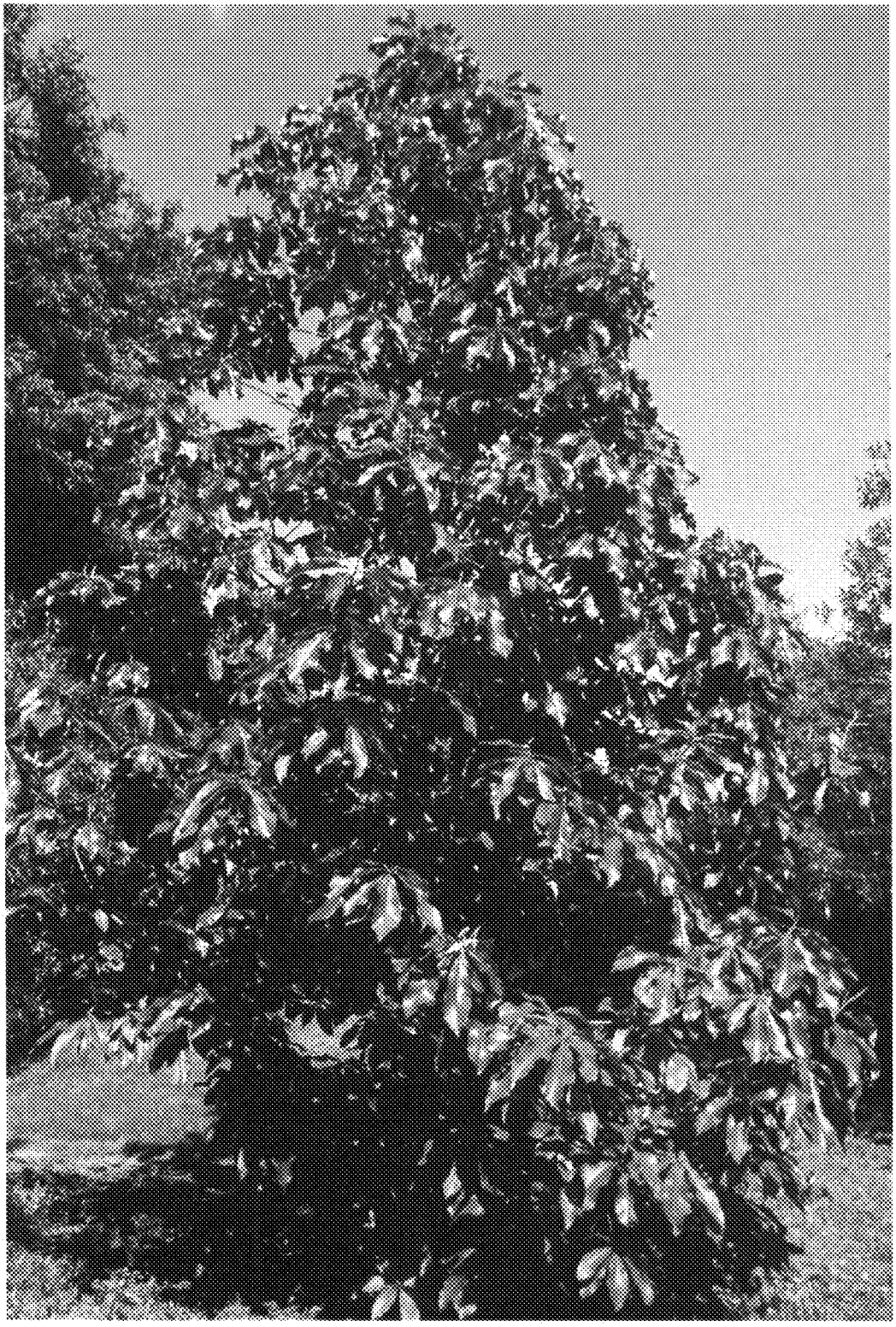
FIG. 1, shows the entire plant at age 5 years.
Figure 2:
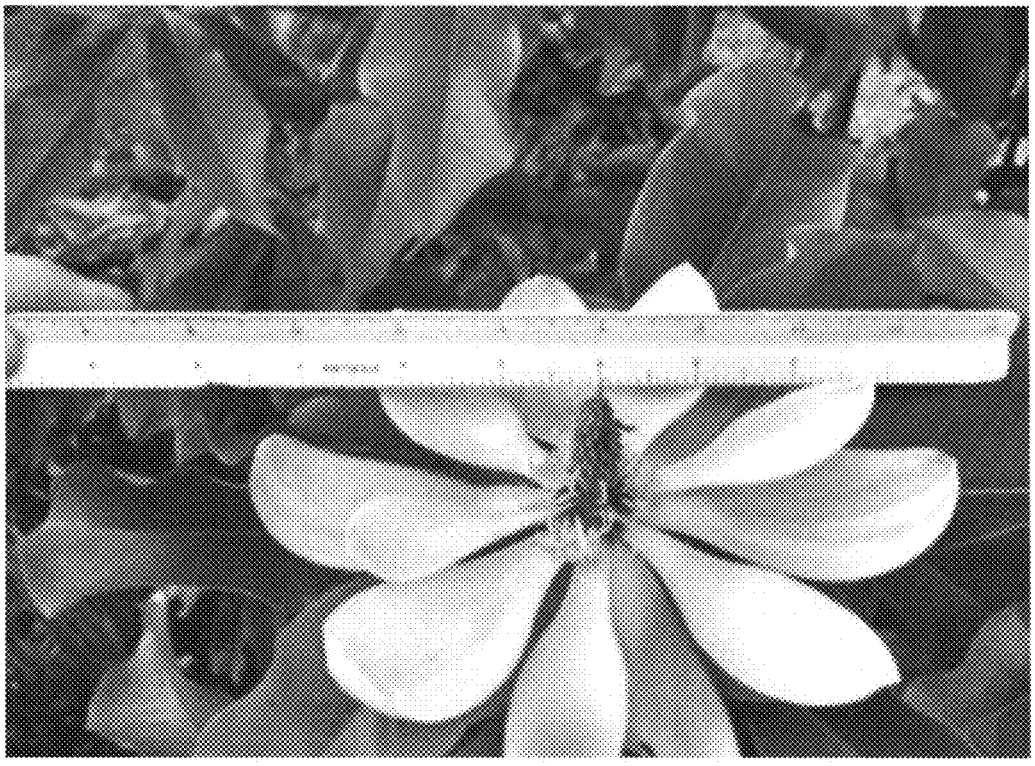
FIG. 2, shows a fully open 'Melissa Parris' flower with a reference engineer's scale.

Plant:

1. *Growth habit.*—Upright tree with dominant central leader (FIG. 1).
2. *Age of plant described.*—5 years; In container 1 year, then ground 4 years.
3. *Height.*—Approximately 6.0 meters.
4. *Spread.*—Approximately 2.5 meters.
5. *Growth rate.*—1.2 meters per year.
6. *Branching characteristics.*—Single trunked tree, with ascending lateral branches forming at varying acute angles, 45-80 degrees to the trunk.
7. *Length of primary lateral branches.*—2-3 meters.
8. *Diameter of primary lateral branches.*—Approximately 2 cm.
9. *Quantity of primary lateral branches.*—46.
10. *Branch arrangement.*—Alternate.
11. *Color and texture of bark on current season's lateral branch.*—Dark Brown (RHS 200C); Smooth with scattered, orange brown (RHS 173D), 0.03 cm lenticles.

Trunk:

1. *Diameter.*—7 centimeters after 5 years.
2. *Texture.*—Moderately smooth with fine, sinuous, vertical striations.
3. *Color.*—Grey (RHS 157D) with prominent pale grey (RHS 159D) lenticels.

Foliage:

Leaf:

1. *Type.*—Simple/single.
2. *Arrangement.*—Alternate.
3. *Retention.*—Tardily deciduous; Leaf dehiscence by Mid-December in Spartanburg, S.C.
4. *Quantity.*—7-10 clustered tightly within 5-7 centimeters at terminal end of each growth flush.
5. *Average length.*—Approximately 27 cm.
6. *Average width.*—Approximately 9 cm.
7. *Shape of lamina.*—Obovate.
8. *Apex.*—Acuminate.
9. *Base.*—Cuneate.
10. *Margin.*—Entire.
11. *Texture of top surface.*—Glabrous to slightly coriaceous.
12. *Texture of bottom surface.*—Lightly pubescent.
13. *Leaf internode length.*—Approximately 13 cm at mid-branch.
14. *Color.*—(May-June): Upper Surface, Near RHS Yellow-Green Group 147; Lower Surface, Near RHS Yellow-Green Group 145B. (September-October): Upper Surface, Near RHS 137A, Lower Surface, Near RHS 146C.
15. *Venation.*—Pinnate.
16. *Petiole.*—Approximately 2.54 cm. in length and 0.25 cm. in diameter, with stipular scar covering approximately 40% of overall length. Upper Side of petiole with sun exposure can develop a color near RHS 166A. Petioles of shaded leaves and lower portions of petioles tend to be near RHS 158A.

Flower:

1. *Natural flowering season.*—Mid April-Early June in the Southeastern US.

Figure 3:
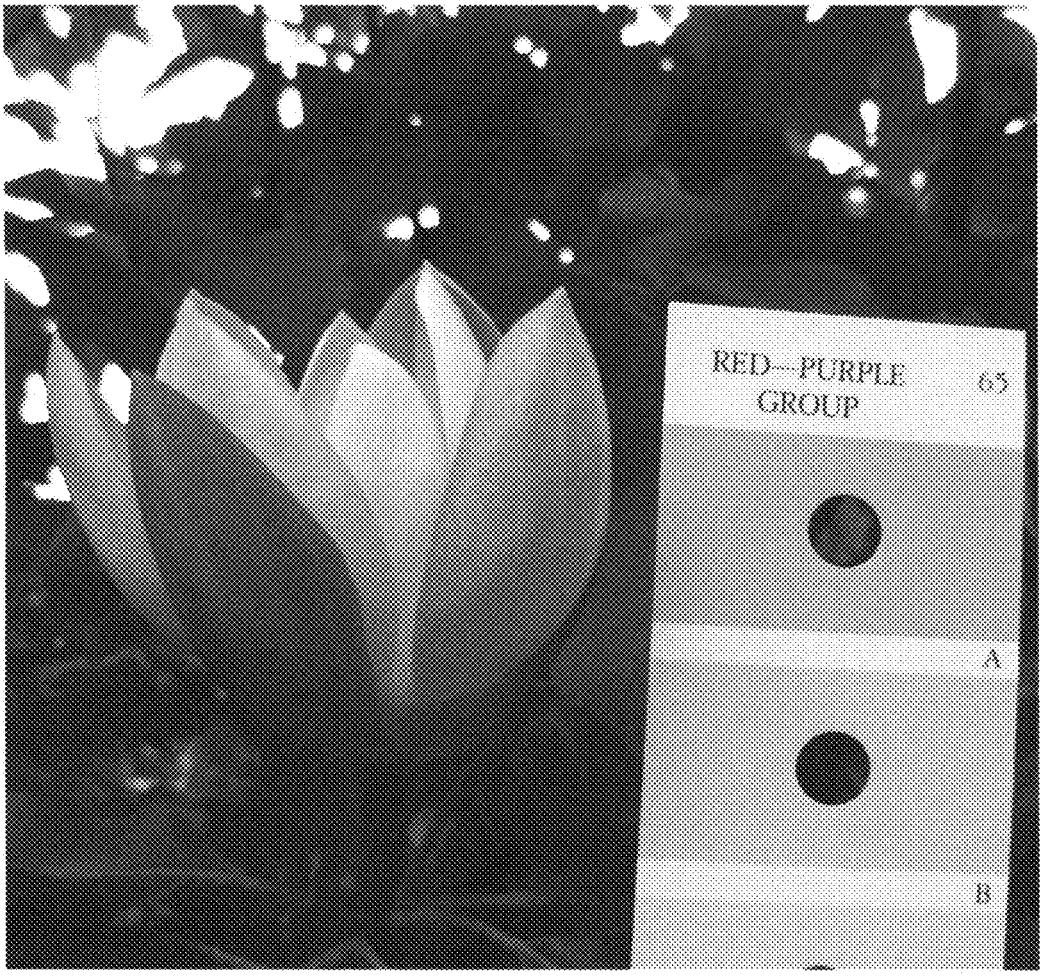
FIG. 3, shows a flower of 'Melissa Parris' with a reference R.H.S. Color Chart; and, FIG. 4, shows a flower of 'Melissa Parris' on the left side with a flower of the pollen parent *M. insignis* 'Anita Figlar' to its right.
Figure 4:
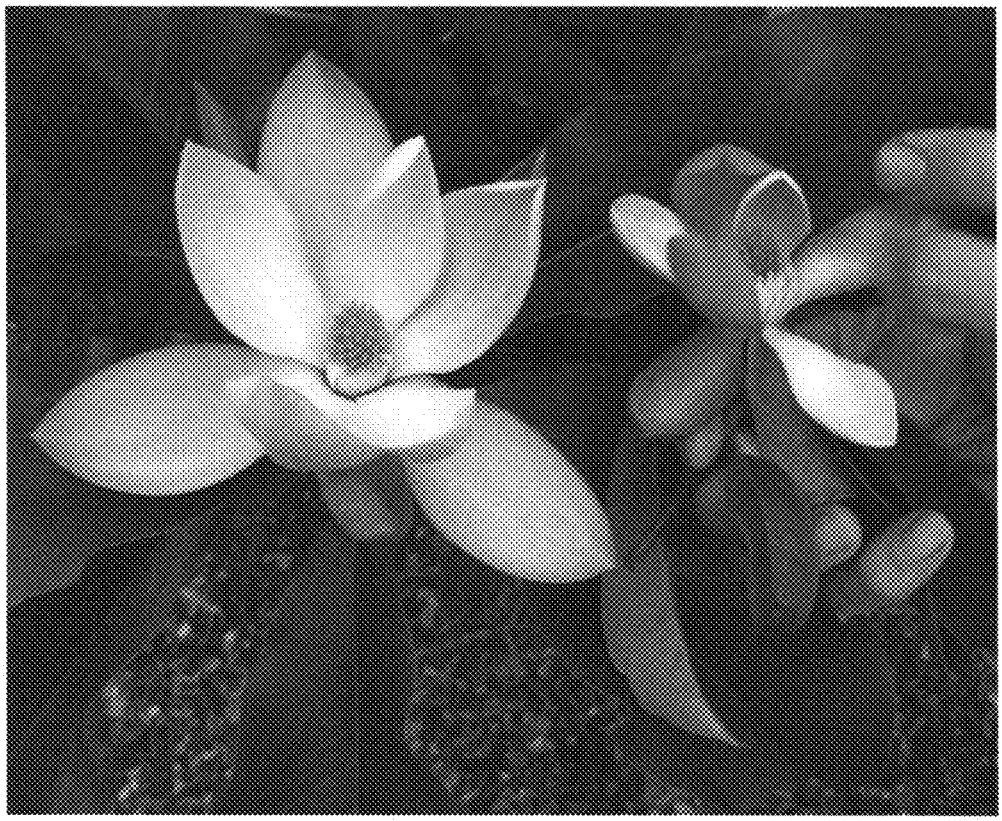

2. *Flowering onset.*—Parent tree first bloomed as a 3 year old seedling. Rooted cuttings have flowered within one year of production.
3. *Flower type and habit.*—Terminal buds initiate flowers that most commonly are displayed singly, but occasionally a subtended companion bud emerges near the completion of flowering of the primary terminal bud.
4. *Flower longevity on the plant.*—Flowers open the first time between 6:30 and 8:00 PM remaining open until early morning when the 6-7 (rarely 9) inner tepals move back into an overlapping position with the 3 outer tepals remaining entirely reflexed. Approximately 24 hours after the first opening, the inner tepals open again more fully than the previous night and shed their stamens. Flowers retain the blend of dark pink (RHS Red-Purple Group 65A) and creamy pink (RHS Red-Purple Group 65B) effectively into the $3^{rd}$ day without looking spent and discolored like many *magnolias* in the post male phase. Flower is self-cleaning. Stamens abscise and shed by the $3^{rd}$ day. Tepals shed before the conclusion of the $3^{rd}$ day or early in the $4^{th}$ day. The 2 days of tepal movements have been observed on cut branches in vases, making the new cultivar 'Melissa Parris' an ideal cut flower specimen.
5. *Quantity of flowers.*—1 in 2014 (3 years post germination); 30 in 2015 (4 years post germination); approximately 100 in 2016 (5 years post germination) on parent tree.
6. *Flower size.*—Diameter — 16-18 cm, while fully open in $2^{nd}$ evening, male phase. Height — 16-18 cm, while closed in $2^{nd}$ day, post female phase.
7. *Flower shape.*—Ovoid when closed in tight bud. Narrow bowl shape in profile when fully open the first evening. Upright tepals form obovoid shape when closed on the second day while three other tepals remain reflexed. Flower assumes a wide bowl shape the second evening and $3^{rd}$ day, when all parts begin to abscise.
8. *Peduncle.*—Length — 3.5-4.0 cm. straight on terminal buds of ascending branches, curved upward on terminal buds of lateral branches. Diameter — Approximately 0.75 cm. Color — Near RHS Yellow-Green Group 147.
9. *Tepals.*—Color — Outer: RHS Red-Purple Group 65A (FIG. 3); Inner: White (RHS N155B) with stations and blends of RHS Red-Purple Group 65A. Arrangement — Alternately whorled, overlapping. Shape — Spatulate — Obovate, Cupped. Size — Length 8.0-9.0 cm, Width — 3.8-4.5 cm at widest point. Margin — Entire. Apex — Obtuse. Base — Short-clawed. Tepal Quantity — 9-12, Commonly 10. Texture — Glabrous on upper and lower surfaces.
10. *Fragrance.*—Intense blend of sweet citrusy fragrances.

Reproductive organs:

Gynoecium: Approximately 1.25 cm. (at widest point)×2.5 cm long.

*Pistils.*—Approximately 40. Stigmatic surface is recoiled when receptive at initial opening and extends along the pistil length approximately 0.2 cm. White (RHS 155D) prior to tepal opening, and Light Orange (RHS 29A) when open.

Androecium: Approximately 0.6 cm. long×0.6 cm. diameter.

*Stamens.*—Exceeding 100. Red (RHS 50B) at basal attachment, White (RHS 155D) from tip, extending approximately ⅔ total length. Stamen length approximately 1.25 cm.

*Pollen.*—Scarce in amount. Light Yellow (RHS 4D) in color.

Other characteristics:

Seeds and fruits: The new cultivar has not proven to be self-fruitful, but fruit and viable seed has been produced from crosses with several *Magnolia* species. Fruit is an aggregate of follicles as typical for *Magnolia* species.

Disease/pest resistance: Neither resistance nor susceptibility to pathogens or pests have been observed.

As herein used, the term "dehisce" refers to splitting or fracturing of an outer membrane to access an interior.

As herein used, the term "tepal" refers to outer flower parts of species having indistinguishable sepals and petals.

We claim:

1. A new and distinct hybrid of *Magnolia* 'Silk Road' x *Magnolia insignis* 'Anita Figlar' named *Magnolia* 'Melissa Parris' as herein illustrated and described.

* * * * *